United States Patent [19]

Grundman

[11] 4,088,749

[45] May 9, 1978

[54] COMPOSITION AND METHOD FOR DETERMINATION OF PREGNANCY

[75] Inventor: Lea Grundman, Jerusalem, Israel

[73] Assignee: Rafa Laboratories Ltd., Israel

[21] Appl. No.: 680,579

[22] Filed: Apr. 26, 1976

[30] Foreign Application Priority Data

May 2, 1975 Israel ..................................... 47223

[51] Int. Cl.$^2$ ..................... G01N 31/00; G01N 33/16
[52] U.S. Cl. ................................... 424/12; 23/230 B; 260/112 R; 424/100
[58] Field of Search ............... 424/3, 8, 12; 23/230 B; 260/112 R

[56] References Cited

U.S. PATENT DOCUMENTS

| | | | |
|---|---|---|---|
| 3,551,555 | 12/1970 | Schuurs | 424/12 |
| 3,639,558 | 2/1972 | Csizmas | 424/12 |
| 3,882,225 | 5/1975 | Patel | 424/12 |
| 3,951,748 | 4/1976 | Devlin | 424/12 X |

OTHER PUBLICATIONS

Bovek, Nature, vol. 191, Sep. 23, 1961, pp. 1293-1294.

*Primary Examiner*—Albert T. Meyers
*Assistant Examiner*—A. P. Fagelson
*Attorney, Agent, or Firm*—Steinberg & Blake

[57] ABSTRACT

Composition for the determining of whether or not a female is pregnant are provided. The composition consists essentially of a neutral and inert particle on which γ-globulin is adsorbed, said γ-globulin being coupled to a bi-functional coupling agent, the two functional groups thereof possessing different reactivities, the other functional group of said coupling agent being coupled to HCG. The body fluid of the female suspected of being pregnant is mixed with the above composition and permitted to stand. Agglutination indicates non-pregnancy whereas failure of agglutination indicates pregnancy.

3 Claims, No Drawings

COMPOSITION AND METHOD FOR DETERMINATION OF PREGNANCY

The present invention relates to a serodiagnostic composition for a method for the determination of pregnancy.

There are known various methods for the determination of pregnancy. Some methods (biological methods) require the use of a specific animal, e.g., rabbits, mice, frogs, etc. These biological tests have serious drawbacks, e.g., they require the availability and housing of many animals meeting specific requirements, which make the method complicated and expensive. Moreover, these methods require special laboratory performances and are usually time consuming, i.e., the results can be obtained only after some days.

It has thus been desirable to develop some methods for the determination of pregnancy which overcome the above drawbacks, i.e., do not require animals, not require any specific laboratory techniques, i.e., can be performed in a physician's office and yield the results in a relatively short time.

It has been found that the best way would be to find a chemical reagent with the help of which said test could be performed.

In Israel Patent Specification No. 16,425 there are described and claimed certain seradiagnostic compositions for the diagnosis of pregnancy. However, there is described only one specific composition which comprises chorionic gonadotropin hormone (CGTH) combined via bis-diazo-benzidine (BDD) with sheep red blood cells and eventually also embodying the CGTH antibody.

However, said known composition is very unsatisfactory as the composition is unstable. It has been tried to overcome said drawback by adding formaline as a stabilising agent. Although the stability of the composition is being improved it is still not satisfactory, as the storage period of the composition obtained is very short, if resuspended in liquid, which is certainly undesirable.

From Israel Patent Specification No. 19,301, German Patent Specification No. 1,808,435 and Dutch Specification No. 66-03,909, there are known serodiagnostic compositions in which HCG is connected to erythrocytes via certain aldehydes and other substances e.g., stabilising agent. The use of such stabilising agent is very undesirable. Moreover, it has been found that the compositions obtained according to the above publications are not very stable.

From Israel Patent Specification No. 34,960 there is known a composition consisting essentially of human chorionic gonadotropin (HCG) coupled to red blood cells by means of glutaraldehyde as coupling agent therebetween. Said composition constitutes a great improvement over the known compositions. However, its drawback is that it still requires quite a long time for the performance of the test. Said drawback may be overcome by certain means. However, even then about 20 minutes are required for the performance of the test. Moreover, the storability of said composition is not entirely satisfactory and could be overcome only by the addition of further materials, e.g., gelatin.

There are known some compositions utilising as basis certain latex particles, the composition of which is kept secret by the manufacturer. However, although they overcome some of the drawbacks set out above they still have some drawbacks. Thus, the agglomerates obtained as the result of agglutination are not very clear and therefore the performance is not always safe. Moreover, said agglomerates do not always appear immediately.

It has, therefore, been desirable to find a composition which overcomes said drawbacks, i.e., which enables the performance of the test in a very short time, the test performed therewith gives clear results which are easy and safe to determine. Moreover, said composition should be well storable.

It has been surprisingly found that in case that $\gamma$-globulin is adsorbed on neutral inert particles (as herein defined) it can be coupled with certain coupling agents to HCG and with the composition obtained the test can be performed within about 3 minutes, giving good and clear results.

The present invention thus consists in a serodiagnostic composition for determining whether or not a female is pregnant, said composition consisting essentially of a neutral-inert particle (as herein defined) on which $\gamma$-globulin is adsorbed, said $\gamma$-globulin being coupled to a bi-functional coupling agent, the two functional groups thereof possessing different reactivities, the other functional group of said coupling agent being coupled to HCG.

Said composition will be called hereinafter HCG sensitized particles.

A neutral-inert particles in connection with the present invention means particles which are neutral and inert towards tho other parts of the composition and which are able to adsorb $\gamma$-globulin in an irreversable manner. Such compounds are for example, polybutadiene, polystyrene, polymerised butadiene styrene, etc. As preferred particles, one may mention polystyrene latex particles.

The preferred by-functional coupling agent is toluene-2,4-diisocyanate (TDIC).

The $\gamma$-globulin may be obtained from any available mamalian or avian serum.

The present invention consists also in the preparation of the composition according to the present invention in which the coupling agent is bound at a low pH and a low temperature to the HCG and the coupling agent-HCG conjugate obtained is linked at an increased pH and temperature to the $\gamma$-globulin adsorbed on the neutral inert particle.

In case that the coupling agent is TDIC the coupling of it to the HCG is performed at about 0°–10° preferably 4° C. (All temperatures herein are indicated in degrees centigrade). The pH for this reaction is between 5.4–7.4 preferably 7.2. The TDIC-HCG conjugate is coupled to the $\gamma$-globulin at about 30°–60°, preferably 40°. The pH for this reaction is between 7.6–9.2 preferably 8.2–8.3.

The concentration of the TDIC conjugate is so chosen as to ascertain the required sensitivity of the test. In case that a polystyrene latex is utilised, said concentration is about 2.5–5 mg/A.g.polystyrene (10 ml suspension of 10%).

The composition according to the present invention is very stable and will not decompose during storage and the conjugate will not be released during the performance of the test.

The present invention also consists in a method for the determination of pregnancy which comprises admixing the aforesaid serodiagnostic composition with an anti HCG serum and a body fluid of a woman suspected to be pregnant. In case that the woman is pregnant, i.e. the HCG is present in the body fluid, the anti HCG serum will react with the free HCG and no reaction will occur between the sensitized HCG particles and the anti serum. Alternatively, i.e., when the woman is not pregnant the anti-serum will cause agglutination after about 3 minutes. Very good, large agglomerates are obtained and the agglutination starts nearly instantly.

The present invention will now be illustrated with reference to the accompanying examples without being restricted by them.

EXAMPLE 1

Preparation of HCG sensitized Latex Particles a. Preparation of γ Globulin of Nornal Rabbit Serum (NRS)

10 ml of serum are put into a beaker of 50 ml which is placed on a magnetic stirrer. Under constant stirring of the serum 6 ml of a saturated $(NH_4)_2SO_4$ solution are added very slowly. The pH is then adjusted to 7.4 by the addition of a 1 N-NaOH solution. Stirring is continued for 30 minutes at room temperature. The contents are put into a centrifuge tube(s) and it is spun down at room temperature 30 minutes at 1,000 × g. The supernatant is discarded. The sediment is dissolved in saline and the volume made up to 10 ml.

The solution is then transferred to a 50 ml beaker. Under constant stirring, as before, 5 ml of saturated $(NH_4)_2SO_4$ solution are added slowly and the pH is adjusted to 7.4. The precipitation is repeated once more by dissolving the precipitate in saline.

The final precipitate is then dissolved in 10 ml of saline and dialysed in the cold, against distilled $H_2O$ under stirring. The next day, the outer fluid is changed to PBS (0.15 M NaCl, 0.01 M phosphate bugger pH 7.2)

$KH_2PO_4$ 0.1 M 132 ml
$NaHPO_4$ 0.1 M 289 ml
NaCl 34,785 g up to 4,210 ml and dialysis is continued for 48 hours with 2 changes of PBS. The outer fluid (dialysate) is checked for the presence of $SO_4^=$ (to 3 ml of disalysate are added an equal volume of $BaCl_2$ 1% and a few drops of HCl 1 N).

When the test for $SO_4^=$ is negative, the contents of the dialysis tubing are centrifuged at 10,000 rpm for 20 minutes in the cold. The supernatant is saved. The concentration of γ-globulin is fixed by OD at 280 μm for computation use $E_{1cm}^{1\%} = 14.6$.

b. Preparation of the TDIC Conjugate 85.2 mg of HCG (obtained from Roussel Uclaf, containing 3.580 units/mg) are dissolved in 3.9 ml of saline. 35.1 ml of phosphate buffer 0.15 M, pH 7.2 are added to the solution which is then cooled in an ice-water mixture. (Said Buffer is comprised of 140 ml of $NaH_2PO_4$ 0.15 M and 360 ml of $Na_2HPO_4$ 0.15 M). 0.78 ml (0,955 g) of toluene-2,4-diisocyanate are added. The solution is incubated for 30 minutes in ice cold water with magnetic stirring, and then centrigued for 20 minutes at 10.000 rpm in a refrigerated centrifuge (0°-4°).

The supernatant is kept for 1 hour in ice and then filtered in the cold through a Whatman glass fibre paper GFLC. The filtrate is divided in aliquots of 2.5 ml and frozen immediately. When necessary the content of a tube is melted and kept in ice until use. The remaining solution is discarded. The TDIC-conjugate is frozen at −18°.

c. Preparation of the senzitized particles

To 10 ml of a latex suspension (Dow-Latex, 0.481 u, Serwa Feinbiochemica Heidelberg) dry substance 10% are added 107.3 ml of a glycine-NaOH buffer. Said buffer having pH 8.28 comprises glycine 7.3 g; NaCl 10.9; and NaOH 1g/liter. (The pH is adjusted to 8.28 by addition of NaOH 1N). To the suspension are added 178.8 ml of γ-globulin of NRS prepared as described in step a diluted previously with glycine-NaOH buffer so as to obtain a concentration of 80-85 μg/ml (Optical density (OD) at 280 nm 0.117-0.124).

The solution is incubated at room temperature with occasional stirring (20°-25°) for 30 minutes. Thereafter it is centrifugated in the cold (4°-8°) for about 5 minutes at 10,000 rpm. The sediment is washed twice with borate saline using each time 300 ml of solution.

The sediment is resuspended in 111.5 ml of borate buffer of pH 8. The suspension is warmed to 40° in a water bath.

The borate buffer is prepared by admixing 12-37 g of $H_3BO_3$ and 8 g of NaCl. To said mixture are added about 250 ml of bidistilled water. 0.52 g of NaOH are added and the pH is adjusted to 8. Thereafter the volume is made up to 8.

The borate saline is prepared by admixing 30 ml of the above borate buffer with 970 ml of saline (NaCl 0.85%).

To the suspension 2.1 ml of TDIC-conjugate prepared as described in step b, are added. The solution is incubated at 40° for 1 hour with occasional stirring and centrifugated as described above. The sediment is washed twice with borate-saline, using each time 300 ml of solution.

The sediment is resuspended in 71.4 ml of borate-saline containing 0.1% of $NaN_3$ and 0.1% of BSA prepared by dissolving 100 mg of $NaN_3$ and 100 mg of BSA in 100 ml of borate-saline, (hereinafter called "reagent I") (BSA stands for crystallized Bovine Albumin of Pentex Biochemicals).

EXAMPLE 2

Preparation of anti-HCG serum 5 ml of a HCG solution having a concentration of 250 μ/ml prepared in phosphate buffer of pH 7.2 said HCG having a potency of 18,000 μ/mg are mixed with 5 ml Complete Freund's Adjuvant (Difco). The mixture is emulsified well.

Each rabbit is injected with 2 ml from the above mentioned emulsion, intradermally into shaved back and limbs at 40 sites, 0.05 m/site. At a separate site 0.5 ml from a crude Bordetella Pertussis Vaccine (32 md. organisms/ml) are injected intradermally.

Blood samples are withdrawn after 3 weeks and at 10 days interval or 3 more times, according to the agglutination titer of the serum. After about 7 weeks the rabbits are bled and the serum is separated by centrifugation and stored in a refrigerator.

Unspecific antibodies are adsorbed from the serum by mixing equal volume of the serum and of washed polymer prepared from Normal Human serum (not containing HCG). The mixture obtained is called "adsorbed anti-HCG".

The obtained serum is diluted in borate saline containing $NaN_3$ 0.1% BSA 0.1% and Ficol 1%. (Ficol is PolyEpichlobydrin 400.000 of Pharmacia Fine Chemicals AB, Uppsala). Said reagent is prepared by dissolving 100 ml of each of the reagents in 100 ml of borate saline. The end point agglutination is checked using a latex sensitized suspension prepared as described in Example 1.

The inhibition of the agglutination is tested with HCG Standard Tablets of Wellcome Reagents Ltd. dissolved in reagent I.

The highest dilution of antiserum which gives a 4+ agglutination in the presence of 50 μl of reagent I and a complete inhibition by 50 μl of HCG standard tablets, as indicated above, containing 1.5 μ/ml is chosen.

EXAMPLE 3

1. One drop of urine of the woman is placed within one of the circles of a slide.
2. One drop of antiserum is added.
3. The two drops are mixed with a glass rod and the slide is rocked for one minute.
4. The one drop of the sensitized latex particles is added.
5. The suspension is mixed again with a clean glass rod. The liquid is spread out so as to fill the area within the printed circle of the slide.
6. The slide is rocked slowly and gently to and from for exactly 2 minutes. The results are read immediately.

Agglutination indicates a negative result, i.e., the woman is not pregnant. A smooth pattern indicates the presence in the urine of minimum 1,500 units of HCG/liter.

EXAMPLE 4

In order to ascertain the sensitivity of the test a composition of the present invention (composition D) was compared with commercial available composition. Said compositions were:

a. Composition of the Applicant called Pregnograph as described in Israel Patent Specification No. 34,960 (Composition A)

b. A latex composition of the Wellcome Foundation Ltd. called Prepurex (Composition B).

c. A latex composition of Organon N.V. called Planotest (Composition C).

The results are shown in Table I

TABLE I

| Exp. No. | No of tests | A Pos | A Neg | D Pos | D Neg | B Pos. | B Neg. | C Pos. | C Neg. |
|---|---|---|---|---|---|---|---|---|---|
| 1 | 20 | 8 | 12 | 8 | 12 | 8 | 12 | 8 | 12 |
| 2 | 47 | 28 | 19 | 28 | 19 | 28 | 19 | 27 | 20 |
| 3 | 34 | 14 | 20 | 14 | 20 | 14 | 20 | 14 | 20 |
| 4 | 46 | 26 | 20 | 26 | 20 | 26 | 20 | 26 | 20 |
| 5 | 57 | 30 | 27 | 30 | 27 | 30 | 27 | 30 | 27 |
| 6 | 28 | 22 | 6 | 22 | 6 | 22 | 6 | 22 | 6 |
| 7 | 59 | 29 | 30 | 29 | 30 | 29 | 30 | 29 | 30 |
| 8 | 67 | 30 | 37 | 30 | 37 | 30 | 37 | 30 | 37 |
| 9 | 82 | 50 | 32 | 50 | 32 | 50 | 32 | 50 | 32 |

The sensitivity of all tests are substantially the same. However the composition according to the present invention has the advantages set out above.

I claim:

1. Method of producing a seriodiagnostic composition for determining whether or not a female is pregnant, said composition consisting essentially of solid neutral particles having γ-globulin adsorbed thereon, said γ-globulin being coupled to one functional group of a bi-functional coupling agent having two functional groups with different reactivities, the other of said functional groups being coupled to human chorionic gonadotropin, which comprises linking one of the functional groups of said coupling agent at a temperature of about 0°–10° C and at a pH of 5.4–7.4 to said human chorionic gonadotropin and then linking said coupling agent at the other of its functional groups at a temperature of about 30°–60° C and at a pH of about 7.6–9.2 to said γ-globulin which has been adsorbed on said neutral particles.

2. The method of claim 1, wherein said neutral particles are of polystyrene latex.

3. The method of claim 1, wherein said coupling agent is toluene-2,4-diisocyanate.

* * * * *